United States Patent [19]

Bayne

[11] Patent Number: 5,586,978
[45] Date of Patent: Dec. 24, 1996

[54] INCONTINENCE DEVICE

[76] Inventor: Donald E. Bayne, 1465 Holton Rd., Muskegon, Mich. 49445

[21] Appl. No.: 335,106

[22] Filed: Nov. 7, 1994

[51] Int. Cl.$^6$ ............................................. A61M 1/00
[52] U.S. Cl. ............................ 604/327; 604/345; 4/144.3
[58] Field of Search .......................... 604/327–331, 604/332, 345; 4/144.3, 144.4

[56] References Cited

U.S. PATENT DOCUMENTS

| | | | |
|---|---|---|---|
| 1,074,368 | 9/1919 | Kutoh | 604/331 |
| 1,682,266 | 8/1929 | Daggy | 603/331 |
| 2,842,129 | 7/1958 | Ernstorff . | |
| 3,194,238 | 7/1965 | Breece, Jr. | 604/329 |
| 3,613,123 | 10/1971 | Langstrom | 4/144.3 |
| 4,559,051 | 12/1985 | Hanson . | |
| 4,601,716 | 7/1986 | Smith . | |
| 4,631,061 | 12/1986 | Martin | 604/318 |
| 4,692,160 | 9/1987 | Nussbaumer | 604/331 |
| 4,702,239 | 10/1987 | Ichikawa . | |
| 4,889,533 | 12/1989 | Beecher | 604/330 |
| 4,904,248 | 2/1990 | Vaillancourt | 604/329 |
| 5,004,463 | 4/1991 | Niggy | 604/327 |
| 5,037,413 | 8/1991 | Haque . | |
| 5,074,853 | 12/1991 | Bryant . | |
| 5,275,592 | 1/1994 | Grizzaffi . | |

FOREIGN PATENT DOCUMENTS

| | | | |
|---|---|---|---|
| 2074875 | 11/1981 | United Kingdom | 604/331 |
| 2091560 | 8/1982 | United Kingdom | 604/330 |

*Primary Examiner*—John G. Weiss
*Assistant Examiner*—Mark O. Polutta
*Attorney, Agent, or Firm*—Price, Heneveld, Cooper, DeWitt & Litton

[57] ABSTRACT

An incontinence device includes a tray having a body with an opening extending through the body, having an annular ring surrounding the opening and extending away from the body to a terminal edge, and having at least one drain to drain material from within the tray body. The annular ring also has an annular groove that opens radially outward from the annular ring. The drain may include an array of slots that extend through the body. The annular groove may be defined between the tray body and an annular flange that extends radially outward from the annular ring at the terminal edge. The annular ring, annular flange, and tray body may be formed in one piece of a moldable material. A liquid barrier having an aperture extending through the barrier may further be included and coupled with the tray body to define a passage through each of the body opening and barrier aperture. An absorbent lining may be interposed between the liquid barrier and the tray body. The tray body may be formed with a concave side defining a hollow that faces away from each of the annular ring and the barrier aperture.

19 Claims, 2 Drawing Sheets

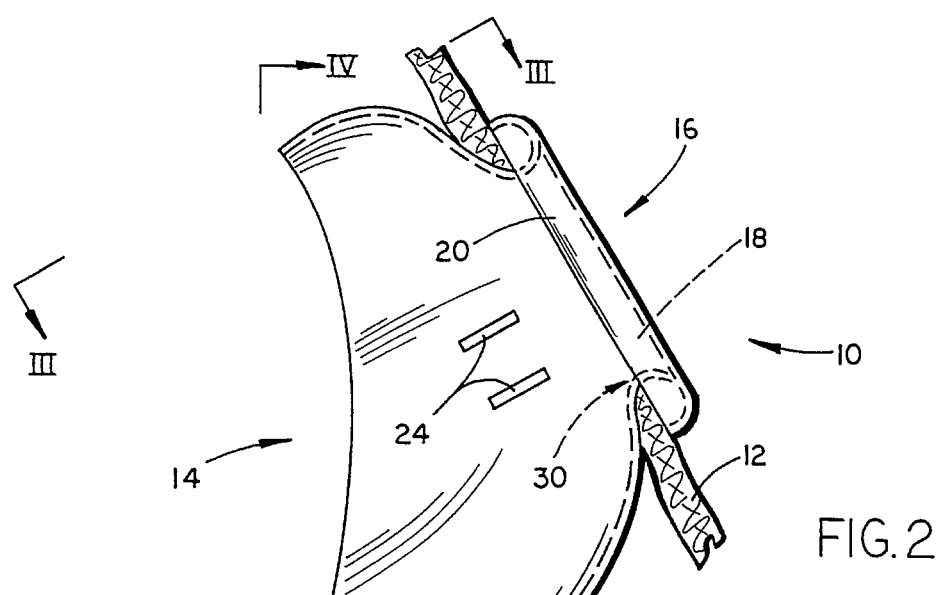
FIG. 2
FIG. 3
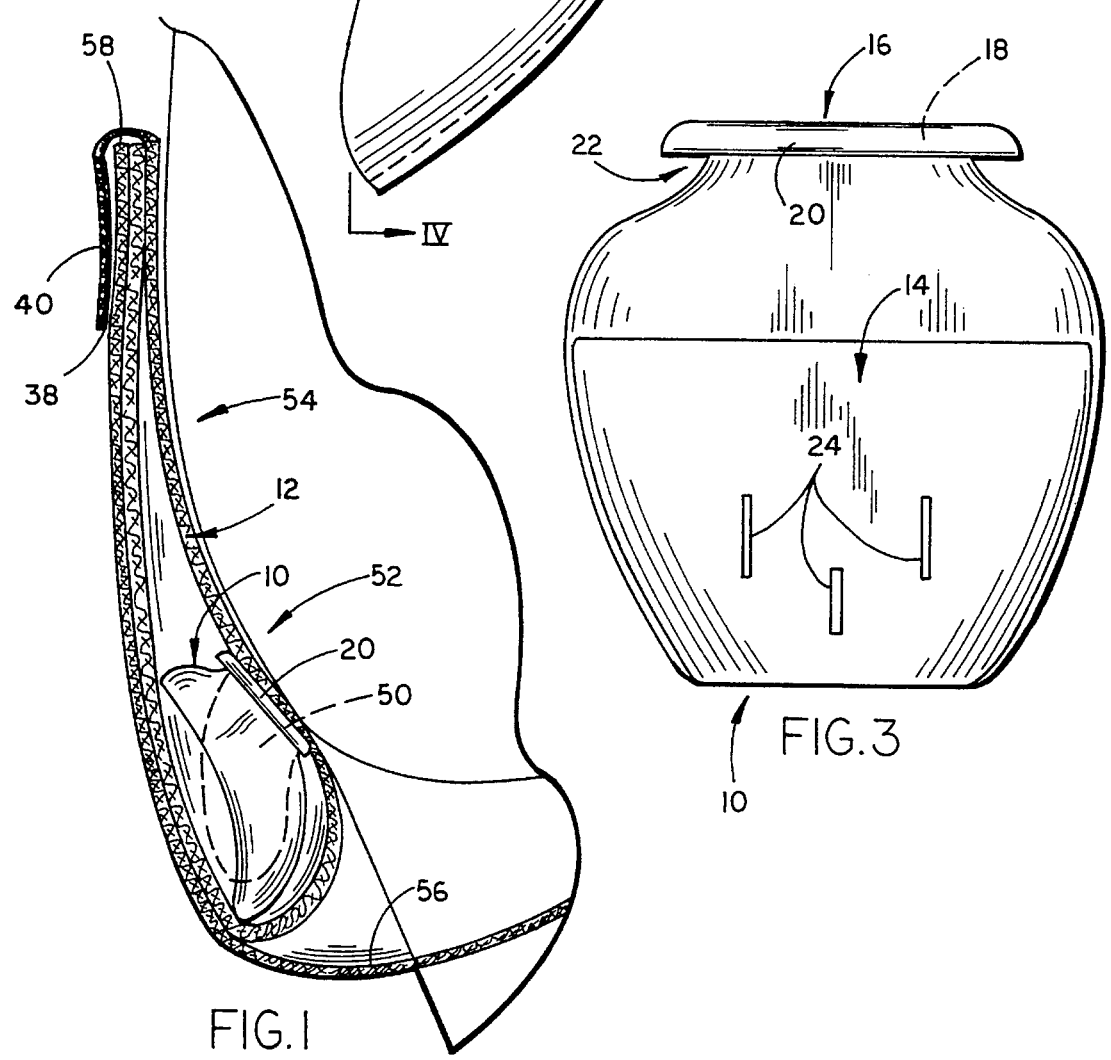
FIG. 1

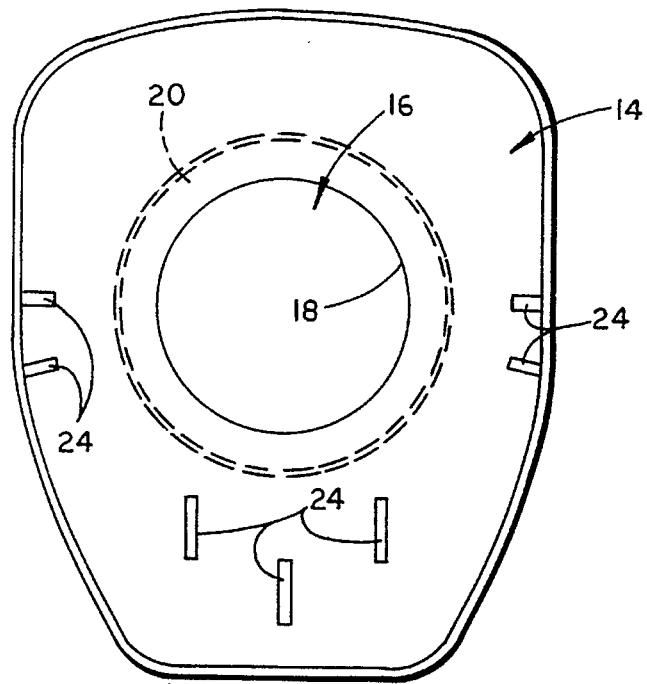
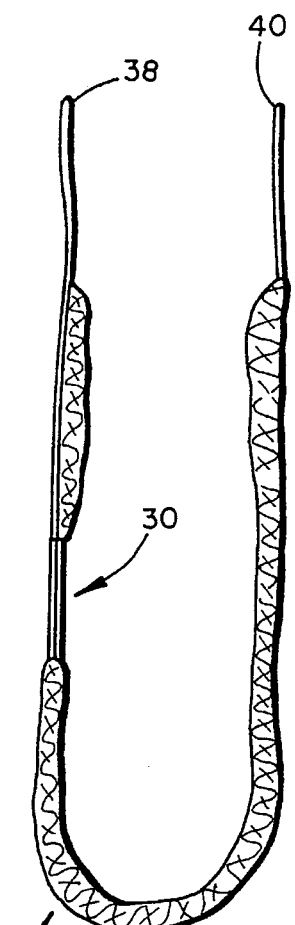
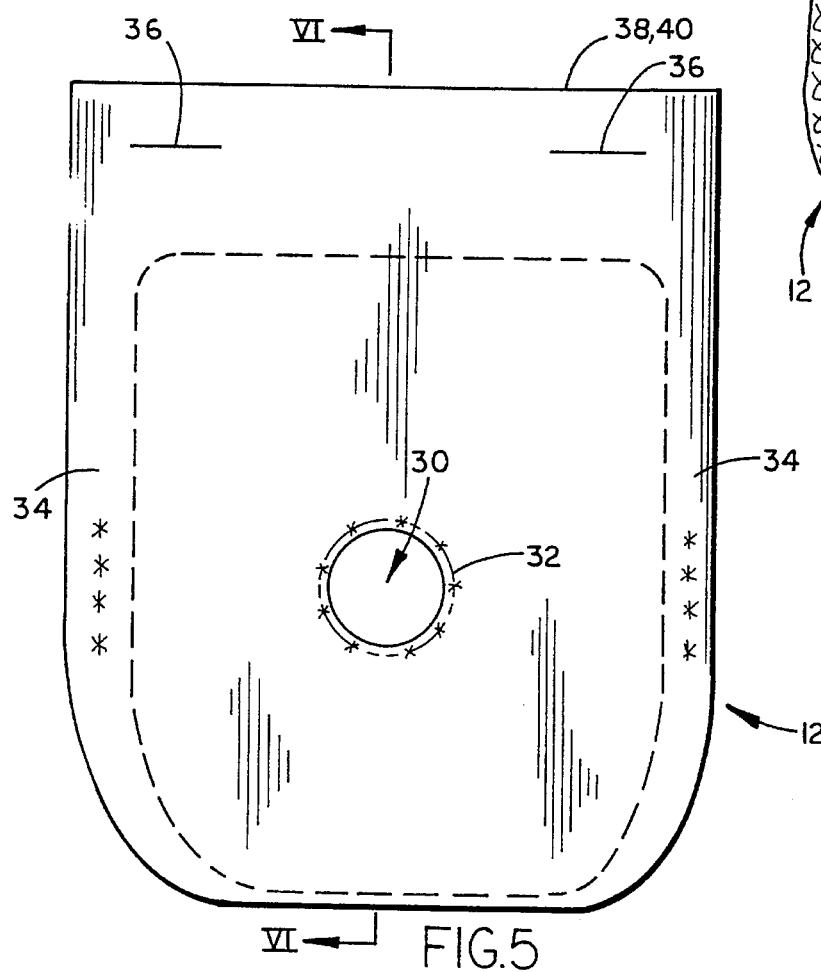

INCONTINENCE DEVICE

BACKGROUND OF THE INVENTION

The invention relates to devices useful in personal hygiene, and is particularly useful for persons having a condition of incontinence.

For various medical reasons, a person may be born with or develop a condition of incontinence. In response, various manufacturers of and companies marketing paper products and others, have developed Various absorbent pad products, basically diapers, for adults. Over time, these absorbent pad products have evolved from simple cloth towels and the like to sophisticated, multi-layered laminated pads, which one may readily find on a variety of store shelves. The current state of adult absorbent pads basically include a multi-layered product of a moisture barrier and a super absorbent layer or filler topped with an open mesh contact layer.

What these known products fail to provide, however, is a clear separation of expelled liquid away from a user's body. Thus, the known devices maintain a moist environment against a user's skin and the user inevitably develops a painful skin rash condition. One may, then, readily understand the need to alleviate the skin rash problem with an improved incontinence device.

SUMMARY OF THE INVENTION

Accordingly, an incontinence device of the present invention provides a clear spacing apart of a user from expelled liquid to minimize, if not eliminate, the formerly inevitable skin rash that persons having an incontinence condition have suffered with the previously known incontinence articles, which inherently manifest a situation of maintaining a moist environment against the user's skin.

An incontinence device according to the present invention includes a tray with body that has an opening extending through the body. An annular ring surrounds the opening and extends away from the body to a terminal edge. The annular ring has an annular groove that opens radially outward from the annular ring. And, the device further includes at least one drain connected to drain material from within the body.

In one aspect of the invention, the tray body may have a concave side defining a hollow. In another aspect of the invention, the incontinence device includes a liquid barrier that has an aperture extending through the liquid barrier. The body is connected with the aperture of the liquid barrier to define a passage through both of the body and the liquid barrier.

In yet another aspect of the invention, the drain includes an array of slots that extend through the body. The annular groove may also be defined by an annular flange that extends radially outward from the annular ring, at the terminal edge of the annular ring. The body, the annular ring, and the annular flange may also be formed in one piece of a moldable material.

In a further aspect of the invention, the liquid barrier is an elongated membrane that extends from a first end and around the tray body to an opposing second end, with the second end being positioned near the first end and the tray body being enveloped by the liquid barrier. An absorbent lining may also be provided and interposed between the liquid barrier and the body of the device.

These and other features, objects, and benefits of the invention will be recognized by those who practice the invention and by those skilled in the art, from the specification, the claims, and the drawing figures.

BRIEF DESCRIPTION OF THE DRAWINGS

FIG. 1 is a fragmentary cross-sectional view showing the invention in use;

FIG. 2 is a side elevational view of an incontinence tray according to the invention;

FIG. 3 is a top plan view of the tray as seen along sight line III—III of FIG. 2;

FIG. 4 is a front elevational view of the tray as seen along sight line IV—IV of FIG. 2;

FIG. 5 is a rear elevational view of an absorbent pad adapted to be used with the tray of FIG. 2; and FIG. 6 is a cross-sectional view along section line VI—VI of the pad of FIG. 5.

DESCRIPTION OF THE PREFERRED EMBODIMENTS

As is generally shown in drawing FIGS. 1–4, an incontinence device according to the invention includes a tray member 10 that is most preferably used in concert with an absorbent pad member 12 (FIGS. 1, 5, and 6).

The tray 10 has a body with a concave side 14 (FIGS. 2–4) defining a hollow. An opening 16 extends through the tray body and connects the hollow with an opposing side of the body. An annular ring 18 surrounds the opening and extends away from both of the body and the concave side 14 of the tray body to a terminal edge. An annular flange 20 extends generally radially outward from the annular ring 18 at the terminal edge and defines an annular groove 22 (FIG. 3) between the annular flange 20 (FIGS. 1–4) and the tray body. The body is also provided with a drain to drain material from within the body. The drain may include an array of slots 24 that extend through the body.

The tray 10 may be formed of any suitable material and is most preferably formed of an easily cleanable and durable material that will promote personal hygiene and sanitary use of the device. Such materials may include various metals, like stainless steel, for example. The tray 10 may be more conveniently formed, however, from various moldable plastics, including polyvinylchloride, for example.

Having described the general configuration of the tray 10, it is noted that the specific dimensions of the tray 10 are generally immaterial, because varying embodiments of the invention may encompass a broad range of differing dimensions. Average dimensions found to be generally suitable for most users follow, however. As viewed in FIGS. 3 and 4, tray 10 may be about 73 mm (2⅞ inches) wide, about 89 mm (3½ inches) tall, about 32 mm (1¼ inch) deep at its top edge, and about 73 mm (2⅞ inches) deep at its bottom edge. The opening 16 through the body of the tray 10 may have an about 35 mm (1⅜ inch) inside diameter, while the annular flange 20 is about 48 mm (1⅞ inch) in outside diameter. For the comfort of the user, the annular flange 20 may be provided with an about 6 mm (¼ inch) radius curvature away from the terminal edge of the opening 16 and toward concave side 14.

The absorbent pad 12 (FIGS. 5 and 6) may be any of the various and generally available adult absorbent pads, or diapers, commonly found on various store shelves, such as is marketed under the trademark Depends™ for example. For use according to the invention, an about 32 mm (1¼ inch) diameter aperture 30 is made in the absorbent pad 12 at a position that is generally centered in the width of the pad 12 and spaced about ⅜ of the length of the pad 12 from one end of the pad. As illustrated in FIG. 1, pad 12 is preferably an elongated membrane that extends from a first end and around tray 10 to an opposing second end, the second end preferably being positioned near the first end.

A pad 12 that is specifically made for use with the incontinence tray 10 is shown in FIGS. 5 and 6. The aperture 30 is positioned as just described above, and is most preferably provided with a heat sealed perimeter edge Further, the opposing side edges 34 of pad 12 are also preferably sealed together at least in the vicinity of aperture 30. To facilitate positioning and securing pad 12 while in use, a pair of "button holes" 36 may be provided near each of two opposing ends 38 and 40 of absorbent pad 12.

In use, the tray 10 will be positioned inside the pad 12 and the annular flange 20 will be inserted through the pad aperture 30 to seat the pad aperture edge 32 in the annular groove 22 of the tray body (FIGS. 1 and 2). The tray 10 and pad 12 so assembled are easily positioned by a male user with insertion of the penis 50 (FIG. 1) into the tray opening 16 and placement of the annular flange 20 against the user's lower abdomen 52. The absorbent pad 12 is oriented with the ends 38 and 40 of the pad 12 extending upward toward the user's waist and the pad 12 laid against the user's abdomen 54. So positioned, the tray 10 and pad 12 assembly is effectively held in place by the user's underbrief 56, preferably with the ends 38 and 40 of the pad 12 extending beyond and folded outward over the waistband 58 of the underbrief 56. Of course, various alternative methods of securing the tray 10 and pad 12 assembly in position for use will occur to those who practice the invention and others. Such alternative methods of securement may include the application of belts, buttons, or pins, for example.

As seen in FIG. 1, the tray 10 separates the absorbent pad 12 and provides a clear or open air space around the penis 50 to separate a damp pad 12 from contacting the user. Thus, the potential for development of an irritated skin rash is greatly minimized, if not eliminated.

It will be understood by those who practice the invention and by those skilled in the art, that various modifications and improvements may be made to the invention without departing from the spirit of the disclosed concept. For example, while the invention is specifically shown in the drawing figures adapted for a male user, the invention may also be adapted for a female user. The scope of protection afforded the invention is, therefore, to be determined by the claims and by the breadth of interpretation allowed by law.

The embodiments of the invention in which an exclusive property or privilege is claimed are defined as follows:

1. An incontinence device comprising:

a tray having a body with an opening that extends through said body;

an annular ring surrounding said opening and extending away from said body to a terminal edge, said annular ring having an annular groove, said annular groove opening radially outward from said annular ring;

a flange extending outward from said annular ring to said terminal edge and defining at least a portion of said annular groove, said flange and annular ring formed as a single piece from a moldable material;

at least one drain operatively connected with said body to drain material from within said tray; and a liquid barrier having an aperture extending through said liquid barrier, said liquid barrier being connected with said tray to define a passage through each of said opening and said aperture said liquid barrier at least partially enveloping said tray.

2. The device defined in claim 1, wherein said drain includes an array of slots extending through said body.

3. The device defined in claim 2, wherein said flange is an annular flange extending radially outward from said annular ring, at said terminal edge, and defining said annular groove between said annular flange and said body.

4. The device defined in claim 3, wherein said body, said annular ring, and said annular flange are formed in one piece of a moldable material.

5. The device defined in claim 4, wherein said tray has a concave side defining a hollow, said tray being oriented with said concave side facing away from said aperture in said liquid barrier.

6. The device defined in claim 4, wherein said tray has a concave side defining a hollow, said opening being operatively connected with said hollow.

7. The device defined in claim 1, wherein said tray body and said annular ring are formed in one piece of a moldable material.

8. An incontinence device comprising:

a tray having a body with an opening that extends through said body;

an annular ring surrounding said opening and extending away from said body to a terminal edge, said annular ring having an annular groove, said annular groove opening radially outward from said annular ring;

an annular flange extending radially outward from said annular ring, at said terminal edge, and defining said annular groove between said annular flange and said body, wherein said body, said annular ring, and said annular flange are formed in one piece of a moldable material;

at least one drain operatively connected with said body to drain material from within said tray, wherein said drain includes an array of slots extending through said body; and a liquid barrier having an aperture extending through said liquid barrier, said liquid barrier being connected with said tray to define a passage through each of said opening and said aperture, said liquid barrier being an elongated membrane member that extends from a first end and around said tray to an opposing second end, said second end being positioned near said first end, wherein said tray has a concave side defining a hollow, said tray being oriented with said concave side facing away from said aperture in said liquid barrier.

9. The device defined in claim 8, further including an absorbent lining interposed between said liquid barrier and said body.

10. An incontinence device comprising:

a tray having a body with an opening extending through said body and having a concave side defining a hollow;

an annular ring surrounding said opening and extending in a direction away from said body to a terminal edge, said annular ring located on a side of said body opposite said hollow and having an annular groove opening radially outward from said annular ring;

a flange member extending outward from said annular ring to said terminal edge and defining at least a portion of said annular groove, said annular ring and said flange member formed as a single piece from a moldable material;

at least one drain operatively connected with said body to drain material from within said hollow of said tray wherein said tray includes an array of slots extending through said body;

a liquid barrier having an aperture therein connected to said opening in said tray to define a passage, said liquid barrier being an elongated membrane member that extends from a first end and around said tray to an opposing second end, said second end being positioned near said end wherein said tray is oriented with said concave side facing away from said aperture in said liquid barrier.

11. The device defined in claim 10, wherein said flange member is an annular flange extending radially outward from said annular ring, at said terminal edge, and defining said annular groove between said annular flange and said body.

12. The device defined in claim 11, wherein said body, said annular ring, and said annular flange are formed in one piece of a moldable material.

13. The device defined in claim 12, wherein said opening is operatively connected with said hollow.

14. The device defined in claim 10, further including an annular flange extending radially outward from said annular ring, at said terminal edge, and defining said annular groove between said annular flange and said body.

15. The device defined in claim 10, wherein said body and said annular ring are formed in one piece of a moldable material.

16. An incontinence device comprising:

a tray having a body with a concave side defining a hollow and having an opening extending through said body;

an annular ring surrounding said opening, located on a side of said body opposite said hollow, extending in a direction away from said hollow, and extending from said body to a terminal edge;

a flange member extending generally radially outward from said terminal edge;

an annular flange extending radially outward from said annular ring, at said terminal edge, and defining an annular groove between said flange member and said body, wherein said body, said annular ring, and said flange member are formed in one piece of a moldable material;

at least one drain operatively connected with said body to drain material from said hollow, wherein said drain includes an array of slots extending through said body; and a liquid barrier having an aperture extending through said liquid barrier, said liquid barrier being connected with said tray to define a passage through each of said opening and said aperture, wherein said liquid barrier is an elongated membrane member that extends from a first end and around said tray to an opposing second end, said second end being positioned near said first end, wherein said body is oriented with said concave side facing away from said aperture in said liquid barrier.

17. The device defined in claim 16, further including an absorbent lining interposed between said liquid barrier and said body.

18. An incontinence device comprising:

a liquid barrier having an aperture extending through said liquid barrier;

a tray having a body with a concave side defining a hollow, having an opening extending through said body, and having at least one drain operatively connected with said body to drain material from said hollow, said tray being connected with said liquid barrier to define a passage from said hollow, through said opening, and through said aperture, said tray being oriented with said concave side facing away from said liquid barrier, wherein said tray includes an annular ring surrounding said opening and extending through said aperture, wherein said annular ring has an annular groove, said annular groove opening radially outward from said annular ring, wherein said aperture has a perimeter edge, and wherein said perimeter edge is seated in said annular groove, wherein said body and said annular ring are formed in one piece of a moldable material, wherein said drain includes an array of slots extending through said body, wherein said liquid barrier is an elongated membrane member that extends from a first end and around said tray to an opposing second end, said second end being positioned near said first end.

19. The device defined in claim 18, further including an absorbent lining interposed between said liquid barrier and said body.

* * * * *

UNITED STATES PATENT AND TRADEMARK OFFICE
CERTIFICATE OF CORRECTION

PATENT NO. : 5,586,978
DATED : December 24, 1996
INVENTOR(S) : Bayne

It is certified that error appears in the above-indentified patent and that said Letters Patent is hereby corrected as shown below:

Col. 1, line 11, "Various" should be --various--; and

Col. 3, line 7, after "edge" insert --32.--

Signed and Sealed this

Twenty-fourth Day of June, 1997

Attest:

BRUCE LEHMAN

*Attesting Officer*  *Commissioner of Patents and Trademarks*